United States Patent [19]

Cutmore

[11] Patent Number: 5,369,369
[45] Date of Patent: * Nov. 29, 1994

[54] DETERMINATION OF CARBON IN A FLY ASH SAMPLE THROUGH COMPARISON TO A REFERENCE MICROWAVE ATTENUATION AND PHASE SHIFT

[75] Inventor: Nicholas G. Cutmore, Woronora Heights, Australia

[73] Assignee: Commonwealth Scientific and Industrial Research Organisation, Campbell, Australia

[*] Notice: The portion of the term of this patent subsequent to Jan. 5, 2010 has been disclaimed.

[21] Appl. No.: 930,399

[22] PCT Filed: Mar. 20, 1991

[86] PCT No.: PCT/AU91/00108

§ 371 Date: Sep. 14, 1992

§ 102(e) Date: Sep. 14, 1992

[87] PCT Pub. No.: WO91/14936

PCT Pub. Date: Oct. 3, 1991

[30] Foreign Application Priority Data

Mar. 23, 1990 [AU] Australia .................. PJ 9287

[51] Int. Cl.$^5$ .............................................. G01N 22/00
[52] U.S. Cl. .............................. 324/637; 324/639; 324/647
[58] Field of Search ............. 324/637, 639, 641, 642, 324/646, 647; 219/10.55 M

[56] References Cited

U.S. PATENT DOCUMENTS

| | | | |
|---|---|---|---|
| 3,577,071 | 5/1971 | Collins | 324/633 |
| 4,233,559 | 11/1980 | Hoberg et al. | 324/58.5 |
| 4,580,441 | 4/1986 | Sakurai et al. | 73/28 |
| 4,705,409 | 11/1987 | Trerice | 374/45 |
| 4,764,718 | 8/1988 | Revus et al. | 324/58.5 |
| 4,977,377 | 12/1990 | Durrett et al. | 324/640 |
| 5,008,506 | 4/1991 | Asmussen et al. | 219/10.55 M |
| 5,109,201 | 4/1992 | Trerice et al. | 324/642 |
| 5,177,444 | 1/1993 | Cutmore | 324/637 |

FOREIGN PATENT DOCUMENTS

| | | |
|---|---|---|
| 0223747 | 1/1984 | European Pat. Off. |
| 0097416 | 5/1987 | European Pat. Off. |
| 3407819 | 6/1985 | Germany |
| 3635977 | 4/1987 | Germany |
| 2198242 | 6/1988 | United Kingdom |
| 2206213 | 12/1988 | United Kingdom |
| 8900413 | 4/1990 | WIPO |
| 9003568 | 4/1990 | WIPO |

OTHER PUBLICATIONS

Derwent Abstract Accession No. 88-307869/44, Oct. 14, 1987, Zheng et al.

*Primary Examiner*—Kenneth A. Wieder
*Assistant Examiner*—Christopher Tobin
*Attorney, Agent, or Firm*—Leydig, Voit & Mayer

[57] ABSTRACT

An apparatus and method to measure the unburnt carbon content of fly ash. A microwave signal is transmitted through or reflected from a fly ash sample and the attenuation or phase shift of the signal received by a detector/detectors is determined with respect to the incident signal and is used to provide a measure of unburnt carbon content. The detectors may be antennae means which also launch the incident signal or may be a completely separate means. A preferred embodiment comprises a microwave oscillator for launching the microwave signal into a fly ash sample in a microwave resonant cavity. Detectors determine the attenuation of phase shift of the received signal with respect to a signal from a reference microwave resonant cavity by the fly ash sample, and a measurement of the unburnt carbon content is obtained.

30 Claims, 6 Drawing Sheets

DETERMINATION OF CARBON IN A FLY ASH SAMPLE THROUGH COMPARISON TO A REFERENCE MICROWAVE ATTENUATION AND PHASE SHIFT

TECHNICAL FIELD

This invention relates to the measurement of the unburnt carbon content of fly ash produced by a coal fired boiler.

BACKGROUND ART

In the combustion of pulverised coal for steam generation in coal-fired power stations there are certain fixed losses determined for example, by plant design, and certain controllable losses caused by operating under non-ideal conditions. The controllable losses comprise:
 (a) losses due to incomplete combustion of both solids and combustible gases;
 (b) losses due to the need for excess air.

In practice the controllable losses show a minimum as a function of oxygen in the flue gas and it is preferable to operate near this minimum. One way this can be achieved is by basing control of the boiler on the measurement of oxygen and carbon monoxide in flue gas. Most large boilers today are equipped with oxygen analysers which measure $O_2$ at one point in a duct. A problem with these analysers is that the reading is drastically distorted by air infiltration into the furnace and in the convection passages downstream of the burners. Also, as measurements are made at one point, sampling errors are large.

Carbon monoxide in flue gas stays at very low levels at high excess air and rises as excess air is reduced. Infrared CO analysers are available which direct the IR beam across the stack, thus minimising sampling errors. However, optimising excess air using CO monitors generally produces a large amount of unburnt carbon in the ash, because CO levels are very low at optimum excess air.

An alternative technique is to base control of the boiler on the determination of unburnt carbon in the fly ash. A 500 MW power station burning black coal of 20% ash will produce about 2500 tonnes/hr flue gas, and 37 tonnes/hr fly ash. The carbon content of this fly ash will be normally in the range 2–5 wt % although it may contain up to 15 wt % carbon. Typically the fly ash concentration in flue gas is about 20 g/m$^3$. Present instruments for the determination of the carbon content of the fly ash rely on extracting a sample, typically less than 1 gram, from the duct and analysing this on a batch basis typically at 10–20 minute intervals.

One prior art carbon concentration monitor [Rupprecht and Patashnick Co., Inc, NYSERDA Report 86-2, January 1986] is based on a microbalance and small furnace. The instrument collects a 10–50 mg sample of fly ash from the outlet duct of a boiler and determines the unburnt carbon in this sample from the mass loss after heating at 750° C., this measurement cycle being repeated at approximately 15 minute intervals. One disadvantage of this analysis technique is that it is very difficult to collect a representative sample of such small size, and therefore sampling uncertainty significantly limits the accuracy of the unburnt carbon determination. The analysis accuracy for replicate samples in laboratory tests was approximately ±0.5 wt % at 2.3 wt % carbon.

Another commercially available device [Energy and Environmental Research Corporation, 18 Mason, Irvine, Calif., USA; December 1987] for the determination of unburnt carbon in fly ash collects an approximately 1 gram sample from the duct using an isokinetic sampler and analyses this for unburnt carbon content from the measured surface reflectance of the sample. The sample collection and measurement cycle is repeated at approximately 5 minute intervals. In a plant test of the instrument at the Nefo power plant, Denmark, the analysis accuracy was approximately ±1 wt % at less than 3 wt % carbon and ±0.5 wt % at greater than 3 wt % carbon. The analysis accuracy is limited by sampling uncertainty, due to the sample size and measuring principle (i.e. surface reflectance) used, and the sensitivity of the reflectance measurement to coal type.

A device based on a measurement of the capacitance of a fly ash filled capacitor has been proposed for the determination of carbon in fly ash in Australian Patent 562440. In this arrangement ash is taken from an ash hopper using a screw conveyor, fed into a measuring chamber into the electric field established by the electrodes of a capacitor and the change in capacitance of the capacitor measured, and finally returned to the ash hopper using a second screw conveyor. The bulk density of the ash in the measuring chamber is assumed to be approximately constant, although compensation for variation in the bulk density is possible using a weighing device.

A microwave technique has been proposed for simultaneously reducing and measuring the carbon content in fly ash in U.S. Pat. No. 4,705,409. In this technique ash is taken from an ash hopper and passed through a metallic waveguide. Microwave radiation directed through the guide is preferentially absorbed by the carbon in the fly ash, and the concentration of carbon is determined from measuring the temperature rise of a water wall surrounding the guide. Sufficient microwave power is injected into the guide to burn the excess carbon in the ash and generate a reduced carbon product. One disadvantage of this technique is that the heat conduction out of the guide, and the associated temperature rise in the water wall, is a function of not only the carbon content of the ash but also the chemical characteristics, temperature and heat conduction properties of the ash. These factors need to be taken into account in the calibration and operation of the device.

Nuclear measurement of carbon in fly ash has also been investigated [Steward, R. F., ISA Transactions, (3), 1967, 200–207]. In this technique carbon concentration is correlated with counts of 4.43 MeV gamma rays produced from carbon atoms by the inelastic scatter of neutrons. Using this technique in laboratory measurements on 10 kg fly ash samples the analysis accuracy is repeated as ±0.5 wt % over the range 2–16 wt % carbon.

DISCLOSURE OF THE INVENTION

It is an object of this invention to provide a method and apparatus to measure the unburnt carbon content in fly ash.

Accordingly, in one aspect this invention consists in an apparatus to measure the unburnt carbon content of fly ash comprising means to generate a microwave signal, transmitter means to launch said microwave signal for transmission through a fly ash sample, receiver means to receive a signal passed through the sample and processing means to determine the attenuation or phase shift of the signal passed through the sample with respect to the launched signal and to produce a measure of unburnt carbon content.

In a second aspect this invention consists in an apparatus to measure the unburnt carbon content of fly ash comprising means to generate a microwave signal, antennae means to launch a microwave signal into a fly ash sample and to receive a reflected signal and processing means to determine the attenuation or phase shift of the reflected signal with respect to the launched signal and to produce a measure of unburnt carbon content.

In a third aspect this invention consists in a method of measuring the unburnt carbon content of fly ash comprising the steps of launching a microwave signal into a fly ash sample, receiving the transmitted signal, determining the attenuation or phase shift of the received signal with respect to the launched signal and producing a measure of unburnt carbon content from said attenuation or phase shift.

In a fourth aspect this invention consists in a method of measuring the unburnt carbon content of fly ash comprising the steps of launching a microwave signal into a fly ash sample, receiving a component of the signal reflected from the sample, determining the attenuation or phase shift of the reflected signal with respect to the launched signal and producing a measure of unburnt carbon content from said attenuation or phase shift.

In one preferred form of the invention separate microwave transmitters and receivers are used. These are provided with suitable antennae, for example, horns or microstrip radiators in an open system, and capacitative or inductive probes in waveguides.

In another preferred form of the invention a single transceiver is used for transmitting and receiving. This arrangement is particularly advantageous where a reflected signal is measured but can also be used where a signal transmitted through the sample is measured by utilising a suitable microwave reflector and effecting a double pass of the sample.

The microwave signal can be generated using any suitable microwave oscillator. Preferably the frequency of the microwave signal is in the range of from 1 to 20 GHz.

Although the attenuation of the transmitted or reflected microwave signals has been found to provide a useful measurement of unburnt carbon in fly ash it is presently preferred to use the change in the characteristics of a microwave resonant cavity induced by the presence of a fly ash sample to produce a measure of unburnt carbon.

Accordingly, it is preferred that a measurement chamber in the form of a microwave resonant cavity receives a fly ash sample and the processing means determines from the attenuation or phase shift of the received signal with respect to the launched signal the change in the resonant cavity characteristics induced by the fly ash sample and produces therefrom a measure of unburnt carbon content.

The resonant cavity characteristics determined from the attenuation or phase shift are preferably resonant frequency, transmitted or reflected power at the resonant frequency, and Q-factor. These are preferably determined from a swept frequency measurement. The presently preferred technique utilises a swept frequency measurement of attenuation.

In a preferred technique two microwave resonant cavities are utilised. The fly ash sample is placed in or passed through one microwave resonant cavity and the other provides a reference measurement. In a further preferred technique a single microwave resonant cavity is used to provide both a reference measurement (made when the cavity does not contain the sample) and subsequent measurements when the cavity contains the sample.

The methods and apparatus of this invention can be used to measure unburnt carbon content of collected fly ash samples or of a fly ash sample entrained in the flue gas from a coal fired boiler.

It will be apparent that the method and apparatus of this invention have several advantages over the prior art. The measurements according to this invention are non-destructive and require no special sample preparation. The microwave measurement can be completed almost instantaneously and therefore a continuous measurement of unburnt carbon content can be provided. Further, the method and apparatus of this invention are not limited by sample size and can be used with samples varying from a few grams to tens of kilograms. The ability to analyse large samples allows sampling uncertainty to be reduced and enables improved measurement accuracy. The method and apparatus are also applicable to both collected samples and in situ measurement.

BRIEF DESCRIPTION OF THE DRAWINGS

This invention will now be described, by way of example only, with reference to the accompanying drawings in which.

MODES FOR CARRYING OUR THE INVENTION

Figure 1:
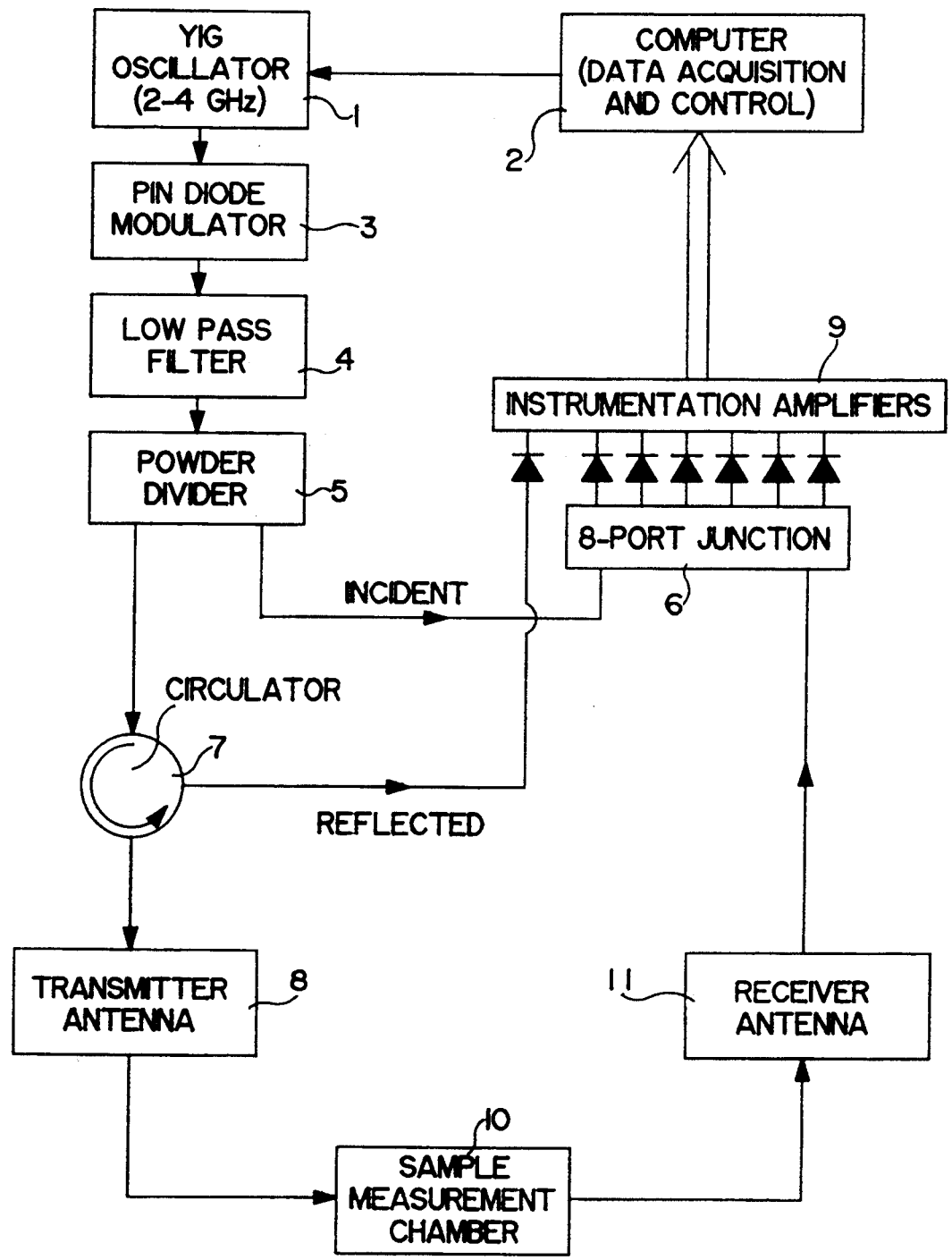
FIG. 1 is a schematic block diagram of an apparatus to measure unburnt carbon in fly ash according to a first embodiment of this invention.

The propagation of an electromagnetic wave (EM) in a dielectric medium is described by Maxwell's equations, and the complex amplitude given by $$E(1) = E_o \exp(-\gamma 1) \tag{1}$$

where l is the distance travelled by the EM wave in the dielectric medium from some reference point where its amplitude was $E_o$, and $\gamma$ is the propagation constant of the wave given by $$\gamma = \alpha + j\beta \qquad (2)$$

where $\alpha$ and $\beta$ are the attenuation and phase constants respectively. For a non-magnetic dielectric medium $\alpha$ and $\beta$ are given by $$\alpha = \frac{2\pi}{\lambda_0} \left[ \frac{\epsilon'}{2\epsilon_0} [(1 + (\epsilon''/\epsilon')^2)^{\frac{1}{2}} - 1] \right]^{\frac{1}{2}} \qquad (3)$$

$$\beta = \frac{2\pi}{\lambda_0} \left[ \frac{\epsilon'}{2\epsilon_0} [(1 + (\epsilon''/\epsilon')^2)^{\frac{1}{2}} + 1] \right]^{\frac{1}{2}} \qquad (4)$$

where $\epsilon_o$ is permittivity of free space, $\lambda_o$ the wavelength is free space, $\epsilon'$ the dielectric constant of the medium and $\epsilon''$ the loss factor of the medium. The attenuation constant $\alpha$ represents the attenuation of the EM wave (in nepers per meter) and the phase constant $\beta$ represents the phase shift of the EM wave (in radians per meter).

From equations (3) and (4), it can be seen that the attenuation and phase shift of an EM wave in a dielectric is a function of the complex permittivity of the medium, $$\epsilon^* = \epsilon' - j\epsilon'' \qquad (5)$$

For a multicomponent dielectric medium the complex permittivity may be approximated by $$\epsilon^*_{medium} = \left( \sum_i v_i \sqrt{\epsilon^*_i} \right)^2 \qquad (6)$$

where $v_i$ and $\epsilon^*_i$ are the volume fraction and complex permittivity of the $i^{th}$ component respectively.

When a plane EM wave is incident upon a dielectric interface, part of it is reflected and part transmitted. For a non-magnetic dielectric in air the reflection coefficient, R, and transmission coefficient, T, are given by $$R = \frac{E_R}{E_0} = \frac{1 - \sqrt{\epsilon^*/\epsilon_0}}{1 + \sqrt{\epsilon^*/\epsilon_0}} \qquad (7)$$

$$T = \frac{E_T}{E_0} = 1 + R \qquad (8)$$

where $E_o$, $E_R$ and $E_T$ are the incident, reflected and transmitted electric field vectors. From equations (3) and (4) it can be seen that the phase shift and attenuation of a transmitted microwave signal are functions of the effective complex permittivity of the sample given by equation (6). For fly ash the complex permittivity of the unburnt carbon is significantly different from the remaining matrix which principally comprises oxides of silicon, aluminium and iron. Therefore the measured attenuation and phase shift for fly ash are strong functions of the unburnt carbon cshift of a reflected signal are therefore also functions of the unburnt carbon content of the samples.

For a cylindrical microwave resonant cavity the resonant frequency of the microwave cavity, f, can be calculated from, $$f_{n,m,l} = \frac{c}{2} \left[ \left( \frac{p}{\Pi a} \right)^2 + \left( \frac{l}{d} \right)^2 \right]^{\frac{1}{2}} \qquad (9)$$

where 'n,m,l' refer to the particular resonant mode (and correspond to the number of electric field maxima in the standing wave pattern $\phi$, r and z directions), 'a' and 'd' are the cavity radius and length respectively and $p$ is a constant determined for each resonant mode. For a $TM_{010}$ resonant cavity, equation (1) reduces to $$f_{010} = \frac{(2.405)c}{2\Pi a} \qquad (10)$$

When a sample with permittivity $\epsilon^* = \epsilon' - j\epsilon''$ is placed about the axis of a $TM_{010}$ cavity, and the sample radius, $r << a$, it is found that, the change in the resonant frequency, $\Delta f$, and Q-factor, $\Delta 1/Q$, are related to the dielectric properties of the sample by, $$\frac{\Delta f}{f} = \frac{\epsilon' - 1}{2} \cdot V_s \qquad (11)$$

$$\Delta \left( \frac{1}{Q} \right) \approx \epsilon'' \cdot V_s \qquad (12)$$

where $V_S$ is the volume fraction of the cavity filled by the sample. Therefore for a constant volume sample, $\Delta f/f$ is proportional to $\epsilon'$ and $\Delta 1/Q$ is proportional to $\epsilon''$. It follows that for measurements on fly ash in such a cavity, $\Delta f/f$ and $\Delta 1/Q$ are both strong functions of the weight percent unburnt carbon in the fly ash.

In the method for determining unburnt carbon content of fly ash according to one aspect of this invention a microwave signal is directed through a fly ash sample using suitable transmitting and receiving antennae and the attenuation and phase shift of the signal due to the fly ash sample are measured. These are normally calculated as the difference between the attenuation and phase shift determined with the sample and air. To compensate for variation in the density and thickness of the fly ash sample the phase shift and attenuation can be normalised to a unit sample mass per unit area. This is not necessary where the variation in sample density and thickness can be maintained within acceptable limits by a suitable sample presentation system.

To obtain a measure of unburnt carbon content in terms of weight percent (wt %) the attenuation or phase shift data are correlated with wt % unburnt carbon, determined by standard laboratory analysis, using least squares regression and equations of the form:

$$\text{wt \% unburnt carbon} = a_0 + a_1(\phi_c) \qquad (13)$$

$$\text{wt \% unburnt carbon} = b_0 + b_1(A_c) \qquad (14)$$

where $\phi_c$ and $A_c$ are the corrected (compensated for variation in sample density and thickness) phase shift and attenuation respectively, and $a_0, \ldots, b_1$ are fitting constants. The unburnt carbon content may also be determined from a combined measurement of attenuation and phase shift, independent of variation in sample density and thickness, using an equation of the form $$\text{wt \% unburnt carbon} = C_0 + C_1(\phi_m) + C_2(A_m) \qquad (15)$$

where $\phi_m$ and $A_m$ are the measured phase shift and attenuation respectively, and $C_0, \ldots, C_2$ are fitting constants.

In the method for determining unburnt carbon content of fly ash according to another aspect of the invention a microwave signal is directed at a fly ash sample and the reflected signal detected. Either a transceiver or separate transmitting and receiving antennae can be used for transmitting and receiving the microwave signal. As with the transmission method the attenuation and phase shift of the reflected signal are measured and preferably are correlated with wt % unburnt carbon using least squares regression and equations of the same form as (13), (14) and (15).

FIG. 1 schematically shows the arrangement of the apparatus to measure unburnt carbon content of fly ash according to this invention. As shown the apparatus comprises a microwave source which takes the form of a Yttrium-Iron-Garnet oscillator 1 tuneable over the range 2 to 4 GHz and controlled by a data logging computer 2. The output of oscillator 1 is modulated by a PIN diode modulator 3 and directed through a low pass filter 4 to a power divider 5. Power divider 5 diverts a small amount of the microwave signal to an 8-port junction 6 as a reference signal. The remainder of the microwave signal is directed via a circulator 7 to a transmitter antenna 8. Circulator 7 is provided to direct any reflected signal to an appropriate instrumentation amplifier 9 to provide a measurement signal for computer 2. Transmitter antenna 8 directs the microwave signal through a sample measurement chamber 10 to a receiver antenna 11 from which the received signal is directed to 8-port junction 6 and instrumentation amplifiers 9 to provide a measure of the attenuation and phaseshift of the received signal in the known manner. This data is transmitted for processing in the manner described herein.

Figure 2:
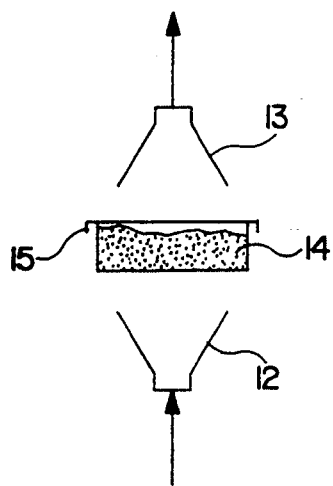
FIG. 2 is a schematic diagram of the antennae and sample measurement chamber in FIG. 1 for measurement in free space.
Figure 3:
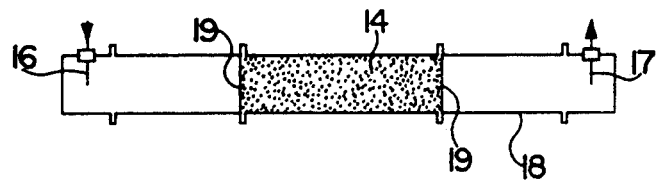
FIG. 3 is a schematic diagram of the antennae and sample measurement chamber in FIG. 1 for measurement in a waveguide.
Figure 4:
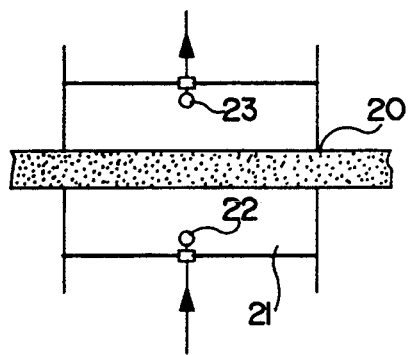
FIG. 4 is a schematic diagram of the antennae and sample measurement chamber in FIG. 1 for measurement in a microwave resonant cavity.

The microwave antennae can be of any type suitable to the selected sample presentation technique. FIGS. 2 to 4 show three preferred arrangements of the antennae and sample measurement chamber.

Referring to FIG. 2, an arrangement for measuring an ash sample in free space is provided. The antennae are horn antennae 12, 13 and the ash sample 14 is contained in a container 15 formed of a material such as wood or plastic which allows the transmission of microwaves. In this arrangement the ash sample 14 is packed in container 15 and suitably positioned between horns 12, 13. The phase shift and attenuation are determined as described above and used to calculate the wt % of unburnt carbon as described above.

FIG. 3 shows an arrangement for measurement on sample in a waveguide. In this arrangement the antennae are capacitive posts or inductive loops 16, 17. The sample 14 to be measured is packed into a section of waveguide 18 of circular or rectangular cross section suited to the frequency range of the microwave signal. For measurements in the 2.6 to 3.95 GHz frequency range an RG-48 rectangular waveguide can be used. The sample is confined to the selected region of the waveguide by plastic sheets 19 which allow transmission of the microwave signal. The phase shift and attenuation are determined as described above and used to calculate the wt % of unburnt carbon as described above.

FIG. 4 shows an arrangement for measurement on a sample in a microwave resonant cavity. In this arrangement the ash sample is contained in a non-conducting, for example, ceramic or plastic tube 20 located along the axis of a TE or TM mode resonant cavity 21. The microwave signal is coupled in and out of the resonant cavity using H-field (inductive loop) probes 22, 23.

Figure 5:
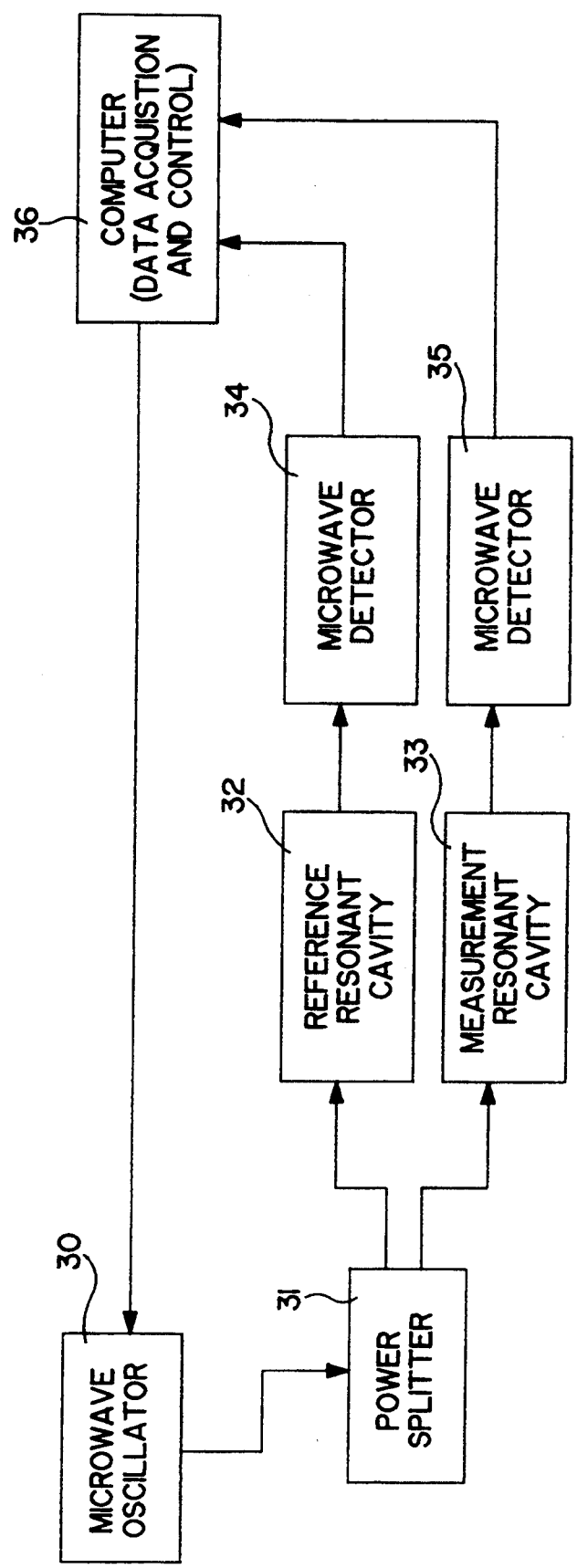
FIG. 5 is a schematic diagram of a further apparatus to measure unburnt carbon content of fly ash according to this invention.

FIG. 5 shows another arrangement for the measurement of the unburnt carbon content of a fly ash sample. A variable frequency microwave oscillator 30 provides a microwave signal to a microwave power divider 31. Power divider 31 produces two output signals which are respectively directed to a reference microwave resonant cavity 32 and a measurement microwave resonant cavity 33. The fly ash sample (not shown) is placed in or appropriately passed through the measurement cavity 33. Detectors 34 and 35 respectively measure the attenuation of the microwave signal respectively propogated in the reference cavity and measurement cavity. Detectors 34 and 35 can be of any suitable known type such as diode detectors. The outputs of detectors 34, 35 are fed to a processor 36 which is used to determine a measure of the resonant frequency, transmitted power at the resonant frequency, and Q-factor of both cavities from the swept frequency response (i.e. attenuation) of the received signal. A measure of weight percent unburnt carbon can then be provided by the processor as explained by the following.

If the resonant frequency and Q-factor of the reference cavity are $f_r$ and $Q_r$ respectively, and the resonant frequency and Q-factor of the measurement cavity are $f_m$ and $Q_m$ respectively, then the weight percent unburnt carbon in the fly ash is determined of the sample bulk density from a function of the form $$\text{Weight Percent Unburnt Carbon} = F\left(\Delta f, \Delta\left(\frac{1}{Q}\right)\right) \qquad (16)$$

$$\text{where}, \Delta f = f_r - f_m \qquad (17)$$

$$\Delta\left(\frac{1}{Q}\right) = \frac{1}{Q_r} - \frac{1}{Q_m} \qquad (18)$$

Typically $$F\left(\Delta f, \Delta\left(\frac{1}{Q}\right)\right)$$

is a correlation function of the form $$\text{Weight Percent Unburnt Carbon} = a_0 + a_1(\Delta f) + a_2\left(\Delta\left(\frac{1}{Q}\right)\right) \qquad (19)$$

where $a_0, a_1, a_2 \ldots$ are fitting constants or, $$\text{Weight Percent Unburnt Carbon} = b_0 + b_1 \left( \frac{\Delta f}{\Delta\left(\frac{1}{Q}\right)} \right) \quad (20)$$

where $b_0, b_1, b_2 \ldots$ are fitting constants

The significant advantages of this arrangement compared to that using a single measurement in a microwave resonator are that the measured $\Delta f$ and $\Delta(1/Q)$ are effectively independent of drifts in the microwave oscillator output frequency due to ambient temperature variations or drift in the oscillator control voltage. This is a consequence of the measurement period of the frequency sweep being much less than the period over which such drifts normally occur. Therefore using this technique high measurement accuracy can be achieved without the need for a highly stabilized microwave source or electronics. This enables $\Delta f$ to be determined from measurement of $\Delta V$, the difference in the control voltage of the microwave oscillator at $f_m$ and $f_r$, rather than from the more difficult and expensive technique of using a microwave frequency counter.

The measured $\Delta f$ and $\Delta(1/Q)$ are independent of temperature drift in the microwave detectors, as such drift only effects the amplitude of the detected microwave signal. If the reference and measurement cavities are substantially similar in design and dimension the measured $\Delta f$ and $\Delta(1/Q)$ are also independent of drifts in the resonant frequency of the cavities due to metal expansion with ambient temperature variations. In this arrangement it is desirable to place a standard absorber in the reference cavity such that $f_r$ is just greater than the maximum $f_m$ that occurs in the particular measurement application. In this case the swept frequency range, $\Delta f$, is minimised.

When the method described above is performed using a single microwave cavity a reference measurement is made when the cavity does not contain the sample. Preferably the period between reference measurements is substantially shorter than oscillator, electronic and temperature drifts.

The apparatus described with reference to FIGS. 1 and 2, FIGS. 1 and 3, and FIGS. 1 and 4 respectively were used to perform measurements on a range of fly ash samples from New South Wales and Queensland power stations. The unburnt carbon content of these samples was determined by standard chemical analysis using LECO analyser and was in the range 0.5 to 13 wt %. For measurement, in free space and in waveguides the samples were packed in an open container to a depth of approximately 100 mm, and in a 200 mm length of RG-48 waveguide section respectively, and the phase shift and attenuation of a 3.3 GHz microwave signal determined. The data were correlated with wt % carbon using the equations, $$\text{wt \% carbon} = a_0 + a_1(\phi_{fly\ ash}/w) \quad (21)$$

$$\text{wt \% carbon} = b_0 + b_1(A_{fly\ ash}/w) \quad (22)$$

where $a_0, \ldots, b_1$ are fitting constant, w is sample mass per unit area (in g cm$^{-2}$) and $\phi_{fly\ ash}$ and $A_{fly\ ash}$ are the phase shift (in degrees) and attenuation (in dB) of the fly ash sample respectively.

The apparatus described with reference to FIG. 5 was also used to perform measurements on one of the fly ash samples. In this case the data were correlated with wt % carbon using equation 19.

R.m.s. errors from correlations on the data using equations (12) and (13) are given below in Table 1.

TABLE 1

| Power Station | Unburnt Carbon (Wt %) | Measurement Geometry | R.m.s. Error Equation (21) | (wt % Carbon) Equation (22) | Equation (19) |
|---|---|---|---|---|---|
| Wallerawang | 3–13 | Free space | 0.41 | 1.41 | — |
| | | Waveguide | 0.28 | 1.22 | — |
| Swanbank | 0.5–5 | Free space | 0.17 | 0.83 | — |
| | | Waveguide | 0.22 | 0.70 | — |
| | | Resonator | — | — | 0.34 |
| Eraring | 0.5–2.5 | Waveguide | 0.19 | 0.29 | — |

Figure 6:
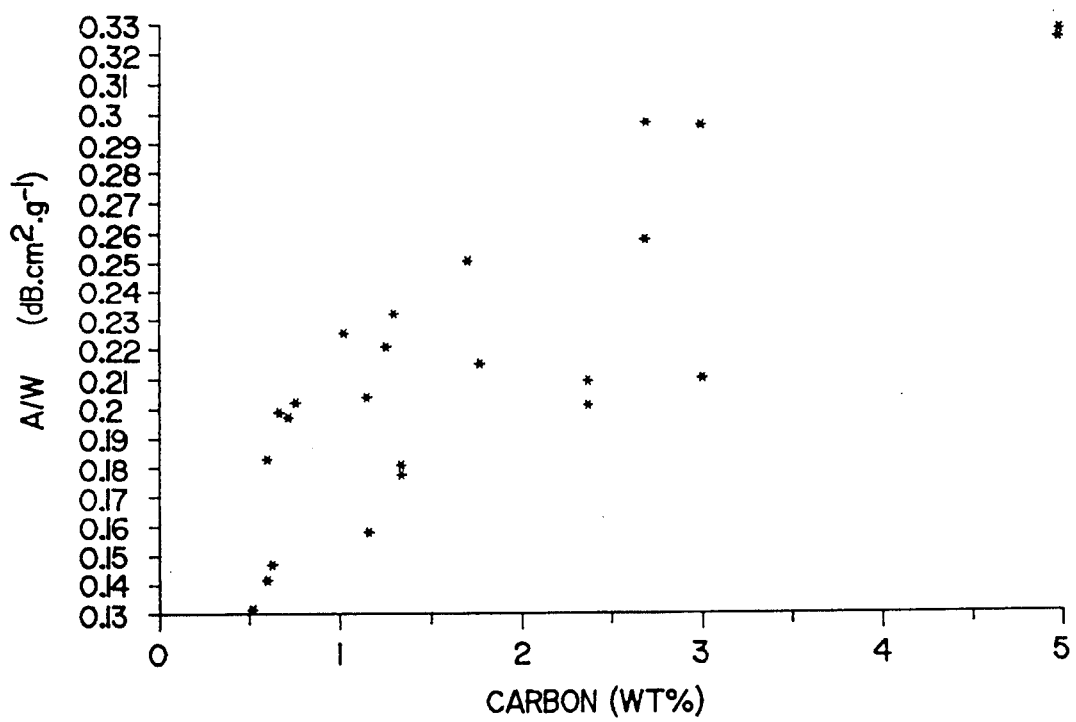
FIG. 6 is a graph showing correlation of (A/W) with wt % carbon for measurement in a waveguide.
Figure 7:
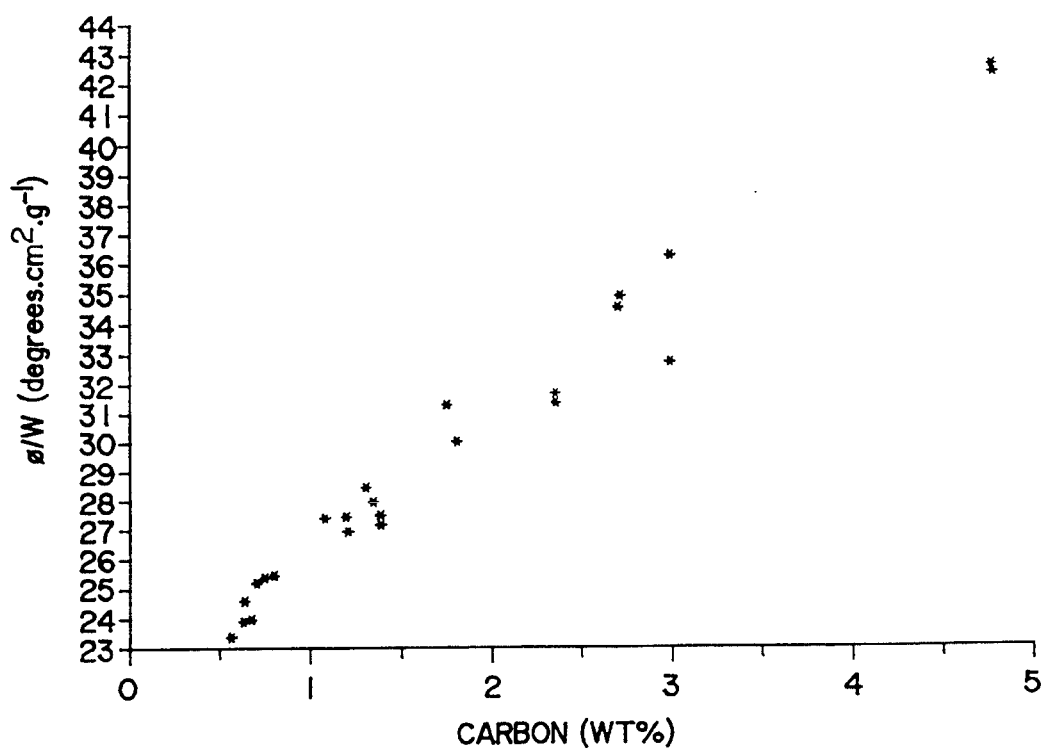
FIG. 7 is a graph showing correlation of ($\phi$/W) with wt % carbon for measurement in a waveguide.
Figure 8:
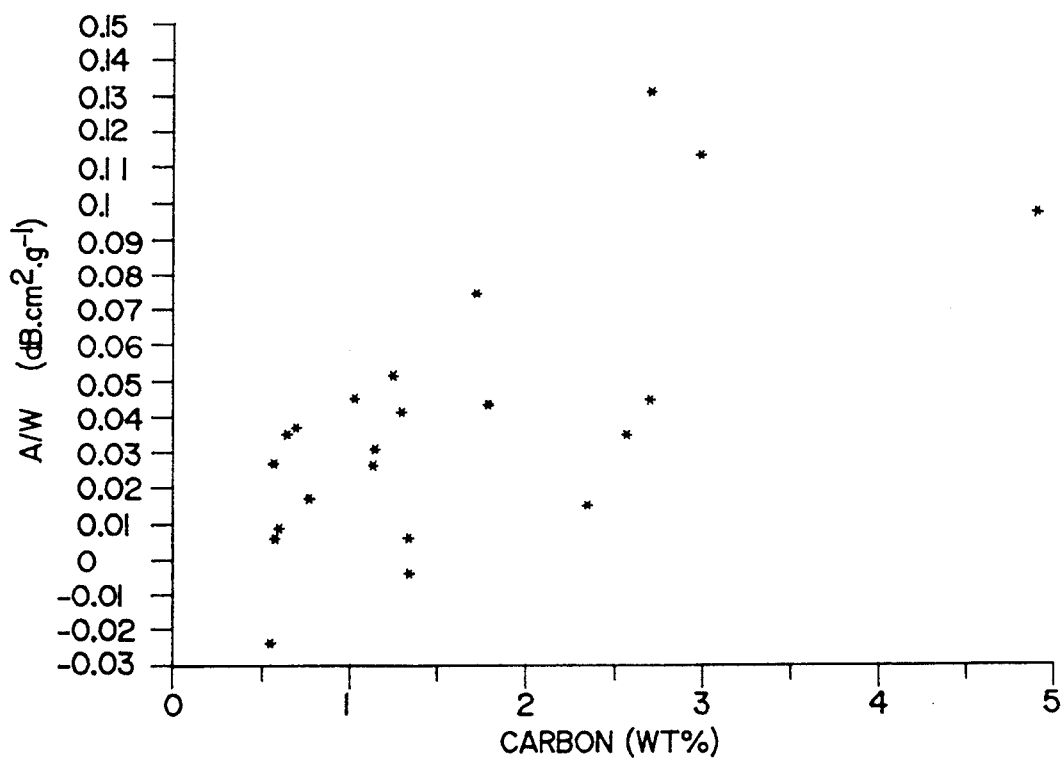
FIG. 8 is a graph showing correlation of (A/W) with wt % carbon for measurement in free space.
Figure 9:
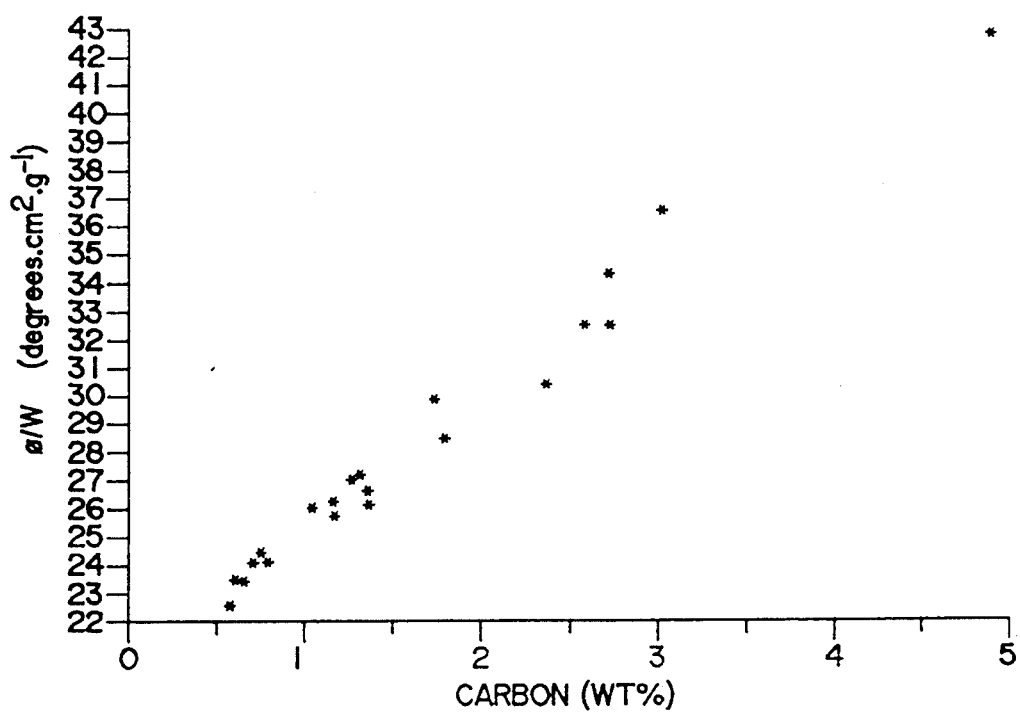
FIG. 9 is a graph showing correlation of ($\phi$/W) with wt % carbon for measurement in free space.
Figure 10:
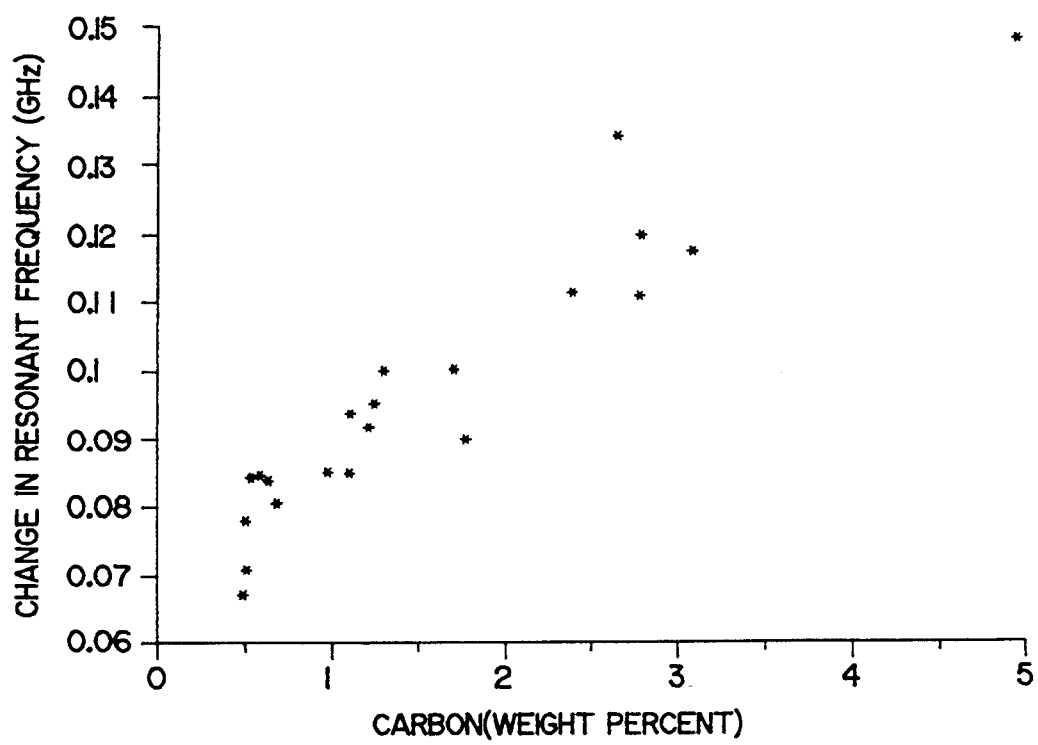
FIG. 10 is a graph showing correlation of change in resonant frequency with wt % carbon for measurements in a resonant cavity.
Figure 11:
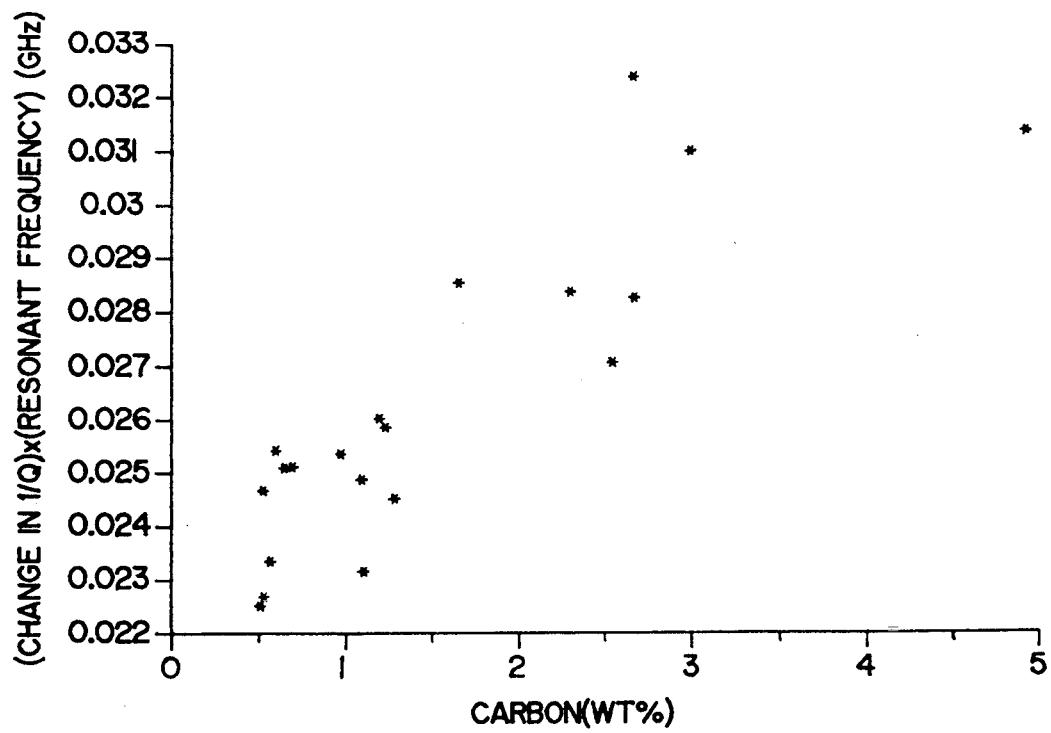
FIG. 11 is a graph showing correlation of (change in 1/Q) x $f_r$ with wt % carbon for measurements in a resonant cavity.

Plots of the data for Swanbank fly ash samples are presented in FIGS. 6 and 7 for measurements in waveguide and FIGS. 8 and 9 for measurements in free space and FIGS. 10 and 11 for measurements in a resonator. The r.m.s. errors in Table 1 represent the total analysis error due to gauge inaccuracy, sampling and chemical analysis. These results indicate that a measurement of phase shift or the resonator characteristics is the most accurate for the determination of carbon content, and the accuracy of analysis is comparable to or better than that obtained with previous methods.

The apparatus described above is particularly suitable for on-line analysis of the unburnt carbon content of fly ash sampled from a boiler outlet duct. Fly ash is removed from the boiler outlet duct by conventional sampling means (not shown), for example using a Cegrit sample and cyclone, and passed through the sample measurement chamber of the apparatus. The fly ash can be fed continuously or in batches, and carried to and from the measurement chamber by any suitable means, for example by a screw conveyor.

The foregoing describes the invention with reference to some specific examples and it will be apparent to those skilled in the art that modifications can be made without departing from the scope of the invention.

I claim:

1. An apparatus to measure the unburnt carbon content of a fly ash sample comprising:
   a reference chamber;
   a measurement chamber for measurement of the fly ash sample;
   means to generate a microwave signal;
   transmitter means to launch the microwave signal for transmission through the reference chamber and the fly ash sample;
   receiver means to receive a signal passed through the sample; and
   processing means for determining the attenuation and phase shift of the signal passed through the sample and the reference chamber with respect to the launched signal and for producing a measure of unburnt carbon content.

2. An apparatus to measure the unburnt carbon content of a fly ash sample comprising:
   means to generate a microwave signal;
   antennae means to launch the microwave signal into the fly ash sample, and to receive a reflected signal; and
   processing means for determining the attenuation and phase shift of the reflected signal with respect to the launched signal, and for measuring the unburnt carbon content of the fly ash, and means for determining a reference measurement of the attenuation and phase shift without the fly ash sample.

3. The apparatus as claimed in claim 1 wherein at least one of the transmitter means and the receiver means include antenna.

4. The apparatus as claimed in claim 2 wherein the antennae means include a single antenna for both launching and receiving the microwave signal.

5. The apparatus as claimed in claim 3, wherein the measurement chamber contains the fly ash sample.

6. The apparatus as claimed in claim 5 wherein the antenna include horn antenna and the measurement chamber includes a material permitting transmission of microwaves.

7. The apparatus as claimed in claim 5 wherein the antenna include inductive loop antenna and the measurement chamber is a section of waveguide.

8. The apparatus as claimed in claim 5 wherein the antenna include inductive loop antenna and the measurement chamber is a section of waveguide.

9. The apparatus as claimed in claim 2 wherein the antenna means include inductive loops.

10. The apparatus as claimed in claim 2 wherein the antenna means include capacitive post antenna.

11. The apparatus as claimed in claim 5 wherein the measurement chamber includes a microwave resonant cavity.

12. The apparatus as claimed in claim 11 wherein the microwave resonant cavity operates in a TE mode.

13. The apparatus as claimed in claim 11 wherein the microwave resonant cavity operates in a TM mode.

14. The apparatus as claimed in claim 11 wherein the fly ash sample is disposed about an axis of the microwave resonant cavity.

15. The apparatus as claimed in claim 2 wherein the microwave signal is launched and received by a microwave transceiver.

16. The apparatus as claimed in claim 15 further comprising a microwave reflector disposed on the distal side of the fly ash sample to the antenna means to reflect the microwave signal passed through the fly ash sample back through the sample to the antenna means.

17. The apparatus as claimed in claim 1 wherein the measurement chamber includes a microwave resonant cavity, and the processing means determines a change in the characteristics of the resonant cavity induced by the fly ash sample and produces therefrom the measure of unburnt carbon content.

18. The apparatus as claimed in claim 17 wherein the change in the characteristics are determined by comparing the signal received by the receiver means with a reference signal obtained from a measurement of the reference chamber not containing the sample.

19. A method of measuring the unburnt carbon content of a fly ash sample comprising the steps of:
launching a microwave signal into a reference chamber and a measurement chamber containing the fly ash sample, receiving the microwave signal;
determining the attenuation and phase shift of the received signal with respect to the launched signal; and
producing a measure of unburnt carbon content from the attenuation and phase shift.

20. A method of measuring the unburnt carbon content of a fly ash sample comprising the steps of:
launching a microwave signal into the fly ash sample;
receiving a component of the signal reflected from the fly ash sample;
determining the attenuation and phase shift of the reflected signal with respect to the launched signal;
correlating a measure of unburnt carbon content with the attenuation and phase shift; and
determining a reference measurement of the attenuation and phase shift without the fly ash sample.

21. The method as claimed in claim 19 including transmitting the microwave signal into the fly ash sample in free space.

22. The method as claimed in claim 19 including disposing the fly ash sample in a waveguide.

23. The method as claimed in claim 19 including disposing the fly ash sample in a microwave resonant cavity.

24. The method as claimed in claim 23 including operating the microwave resonant cavity in a TE mode.

25. The method as claimed in claim 23 including operating the microwave resonant cavity in a TM mode.

26. The method as claimed in claim 23 including determining the measure of the unburnt carbon content of the fly ash sample from a change in the characteristics of the microwave resonant cavity induced by the fly ash sample.

27. The method as claimed in claim 26 including determining the change in the characteristics of the microwave resonant cavity by comparing the received signal with a reference signal passed through the reference chamber.

28. The apparatus as claimed in claim 1 wherein the transmitter means and the receiver means include antenna.

29. The apparatus as claimed in claim 1 wherein the processing means determines the change in the characteristics of the resonant cavity induced by the fly ash sample and produces therefrom the measure of unburnt carbon content.

30. The method as claimed in claim 15 including transmitting the microwave signal into the fly ash sample in free space.

* * * * *